United States Patent [19]

Edeling et al.

[11] Patent Number: 4,609,508
[45] Date of Patent: Sep. 2, 1986

[54] METHOD FOR THE MANUFACTURE OF IMPLANTABLE ELECTRODES OF VITREOUS CARBON

[75] Inventors: Martin Edeling, Erlangen-Frauenaurach; Konrad Münd, Uttenreuth; Raghavendra Rao, Erlangen; Erhard Weidlich, Spardorf, all of Fed. Rep. of Germany

[73] Assignee: Siemens Aktiengesellschaft, Berlin and Munich, Fed. Rep. of Germany

[21] Appl. No.: 659,442

[22] Filed: Oct. 10, 1984

[30] Foreign Application Priority Data

Oct. 14, 1983 [DE] Fed. Rep. of Germany ....... 3337470

[51] Int. Cl.[4] ............................................. B29C 39/10
[52] U.S. Cl. .................................... 264/29.6; 128/642; 264/29.7; 264/85; 264/105; 264/259; 264/272.13; 264/337
[58] Field of Search ................ 264/29.5, 29.1, 29.6, 264/29.7, 259, 272.13, 105, 337, 85; 128/642

[56] References Cited

U.S. PATENT DOCUMENTS

| | | | |
|---|---|---|---|
| 1,181,811 | 5/1916 | Wallace | 264/104 |
| 2,303,515 | 12/1942 | Toepfer | 264/259 |
| 2,527,294 | 10/1950 | Bailey | 264/104 |
| 2,768,408 | 10/1956 | Strigle, Jr. et al. | 264/337 |
| 3,198,714 | 8/1965 | Johnson et al. | 264/29.7 |
| 3,890,420 | 6/1975 | Neward | 264/272.11 |
| 4,426,368 | 1/1984 | Quella et al. | 264/29.7 |

FOREIGN PATENT DOCUMENTS

| | | | |
|---|---|---|---|
| 2324605 | 12/1974 | Fed. Rep. of Germany | 264/337 |
| 46-41208 | 12/1971 | Japan | 264/29.1 |
| 49-21396 | 2/1974 | Japan | 264/105 |
| 50-24343 | 8/1975 | Japan | 264/104 |
| 438224 | 5/1978 | U.S.S.R. | 264/29.1 |

*Primary Examiner*—Jeffery Thurlow
*Attorney, Agent, or Firm*—Kenyon & Kenyon

[57] ABSTRACT

The invention relates to a method for the manufacture of implantable electrodes of vitreous carbon with an electrode head and an electrode stem, by pyrolysis of cross-linked synthetic resins. Electrodes manufactured in accordance with such a method exhibit high surface quality. In accordance with embodiments of the disclosure, the electrode stem is manufactured in the form of a blank by hardening a resin precondensate, then the electrode head is cast onto the blank in a casting mold, using a resin precondensate, and is cross-linked. Subsequently hardening takes place and then the synthetic resin is converted into vitreous carbon by pyrolysis, and the electrode obtained in this manner may, if desired, be activated to provide the electrode with a microporous surface structure.

17 Claims, 1 Drawing Figure

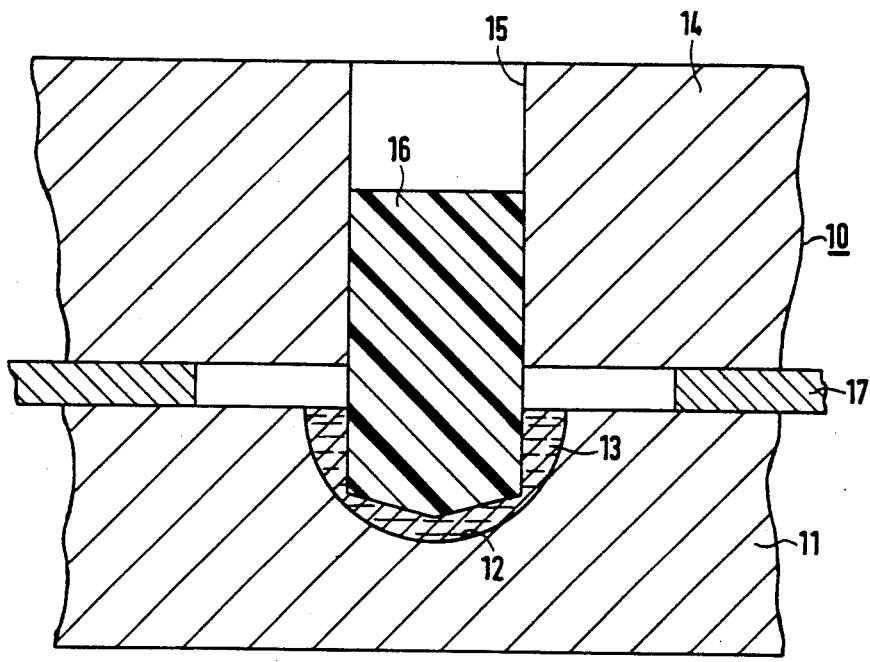

METHOD FOR THE MANUFACTURE OF IMPLANTABLE ELECTRODES OF VITREOUS CARBON

FIELD OF THE INVENTION

This invention relates to a method for manufacturing implantable electrodes of vitreous carbon having an electrode head and an electrode stem by pyrolysis of cross-linked synthetic resins.

BACKGROUND OF THE INVENTION

Electrodes of vitreous carbon are suitable for use as implantable effectors, and as sensors for use in biomedical applications. See, e.g., DE-OS No. 26 13 072. Effectors are intended herein to refer to electrodes through which a stimulating effect is produced; sensors are electrodes with which measurements may be conducted. Examples of effectors are stimulating electrodes for cardiac pacers, as well as electrodes employed to stimulate nerves and muscles. Electrodes employed to make oxygen measurements in the body are referred to herein as sensors.

For implantable electrodes which consist generally of an electrode head and an electrode stem the following requirements are of particular importance and must be met:

Good body compatability,
High capacity and, therefore, low polarization,
Low chronic stimulation threshold rise. Electrodes of vitreous carbon satisfy the two first-mentioned requirements quite well. However, they display a long-term rise in stimulation threshold.

One possible explanation for the rise in stimulation threshold observed in vitreous carbon electrodes is the rough surface of such electrodes. This roughness is caused by the mechanical processing in the manufacture of the electrodes. The present method employed during the manufacture of stimulation electrodes of vitreous carbon consists of the chip-removing shaping of a blank of cross-linked synthetic resin and the subsequent pyrolysis of the electrode body obtained. In addition, the foregoing method is cost-intensive.

It is an object of this invention to provide a simple and inexpensive method which permits the manufacture of implantable electrodes of vitreous carbon which meet all of the requirements for such electrodes specified above.

BRIEF DESCRIPTION OF THE INVENTION

Thus, in accordance with this invention, an electrode stem is fabricated in the form of a blank by hardening a resin precondensate. The electrode head is then cast onto the blank in a casting mold, using a resin precondensate, and is then cross-linked. Subsequently the hardening is performed, and subsequent to that step the synthetic resin is converted pyrolytically into vitreous carbon. Optionally, the electrode prepared in the manner described above is activated.

Advantageously, in accordance with the method of this invention, an electrode head is provided which exhibits a smooth surface, i.e., high surface quality. It has been found that not only do the electrode blanks exhibit a very smooth surface, but, in addition, the smooth surface is largely preserved after pyrolysis. The smooth surface present on the electrode produced by the method of this invention results in a lesser growth of connecting tissue during implantation than is observed during implantation of electrodes which have a rough surface. This, in turn, results in a lower long-term stimulation threshold rise. In addition to high surface quality attained by the electrodes produced in accordance with this invention, the low investment cost is also an advantage of this method of the present invention.

The present method for the manufacture of vitreous carbon electrodes comprises a two-stage casting process. It is known in principle to fabricate molded vitreous carbon bodies of heat-hardenable synthetic resins by shaping, with the use of casting processes, followed by polycondensation and a heat treatment. (See, DE-OS No. 24 00 909, page 3, next to the last paragraph, to page 4, paragraph 1.) The molded bodies are formed stepwise. However, centrifugal casting is employed by the known method, referred to above, because shaped bodies which are manufactured by this method have parts with at least one surface of rotation. In addition, the known method referred to above is employed to manufacture articles of large dimension. However, with reference to the foregoing, there is no mention of the manufacture of implantable electrodes and the high surface quality of the molded bodies produced.

In accordance with the method of the present invention, casting molds of a non-wettable plastic can be employed with advantage. Such plastics, which must be temperature-stable and should have a long shelf-life, include especially polypropylene, polytetrafluoroethylene and silicone. The advantage of plastic casting molds is their ease of manufacture. Preferably, casting molds of silicone are employed, because in such molds the high gas permeability is found to be advantageous, since the water liberated during the condensation reaction can escape in the form of steam through the casting mold.

In accordance with the method of this invention, it is preferred to employ casting molds of alloy steel which are generally hardened and highly polished. Casting molds of alloy steel have the practical advantage that they can be used as many times as desired. In addition, the electrode blanks can be hardened directly in the mold, which means a savings in operational steps. It is of advantage if the casting mold of alloy steel is gold-plated, for then the use of a mold release agent can be dispensed with.

In the method of the present invention, a resin of precondensated furfuryl alcohol is preferably used as the resin precondensate for the fabrication of the electrode stem as well as of the electrode head. However, as an alternative to furfuryl alcohol, precondensates of other resins can be used such as phenolformaldehyde and furane resins. The electrode head blanks are cross-linked within the casting mold. The hardening can be performed inside or outside the mold, while hardening within the mold is preferred.

The invention will be explained in greater detail with reference to an example of an embodiment of the invention and the appended FIG. 1 a cross-sectional view of the casting mold used in electrode manufacture.

If furfuryl alcohol, which can be obtained commercially at a low price and with high purity, is chosen as the starting material for the synthetic resin, the corresponding resin precondensate can be made therefrom by acid or base catalysis. For this purpose, for example, 150 ml furfuryl alcohol is reacted at 50° C. with 5 ml of a 1% solution of p-toluene sulfonic acid in ethanol, and the foregoing components are heated within two hours to a temperature of 90° C. while stirring continuously. The mixture is then held at that temperature for two hours. A resin precondensate is obtained from this process which has a viscosity of about 50 mPa.s at a temperature of 90° C., and is, therefore, still liquid enough to be able to be injected, for instance, into capillaries 1 mm wide. Such a precondensate can be stored for several weeks at room temperature.

In addition to p-toluene sulfonic acid, other (strong) organic acids can be used as hardening catalysts, for instance, other aromatic sulfonic acids, trichloroacetic acid and oxalic acid. The catalyst concentration is generally 0.01 to 1 percent by weight based on the material (for the manufacture of the synthetic resin). The temperature employed during the manufacture of the resin precondensate is generally in the range of about 50° to about 120° C.; the time is between 2 and 16 hours.

As already explained, the electrode blanks are made by a two-stage casting method, the electrode stem being made first. To this end, the resin precondensate is placed in a silicone hose, for instance, with an internal diameter of 2.4 mm and a length of up to 50 cm. The resin precondensate is then cross-linked in the silicone hose at a temperature of 70° to 100° C. within 24 to 48 hours, and is subsequently hardened completely at 150° to 200° C. within 24 hours. The silicone hose is separated from the rod of synthetic resin formed within the hose, and the rod is cut into pieces of suitable length, for instance, 4 mm (diameter: 2.4 mm), which represent the electrode stem blanks.

With reference to FIG. 1, a two-part casting mold 10 is used for the manufacture of the electrode blanks as shown in the Figure. The lower part 11 of this casting mold has a hemispheric recess 12 in the form of an electrode head. This recess is partly filled with resin precondensate 13. The upper part 14 of the casting mold has a hole 15 which serves for receiving the electrode stem blank 16. The upper part 14 is placed on the lower part 11 with the spacing of 0.5 to 1.5 mm, using a spacer 17, and then, the electrode stem blank 16 is inserted into the hole 15 in such a manner that it extends almost to the bottom of the recess 12. If the lower side of the blank 16 is slightly pointed, as can be seen from the Figure, then the electrode stem is wetted uniformly and free of bubbles by the liquid resin precondensate 13. The amount of resin precondensate is chosen so that the hemispheric recess is completely filled after the blank is inserted.

The resin precondensate which is placed in the warmed-up mold is then cross linked within 24 to 28 hours under continuous heating from a temperature of 70° C. to 100° C. Subsequently, the still flexible electrode blank is hardened in air at a temperature of 150° C. to 200° C. (duration: 24 hours), which can be done inside or outside the casting mold.

The two-stage casting method described above has the following advantage over single-step methods in which the electrode stem and the electrode head are cast simultaneously. In the single-step method, the sealing of the two mold parts from each turns out to be a problem. Traces of the resin precondensate always penetrate into the capillary gap between the upper part and the lower part, so that cavities at the transition from the electrode head to the electrode stem are unavoidable. This problem does not exist in the two-stage method.

The conversion of the electrode blanks into the electrodes proper is accomplished by pyrolysis, wherein vitreous carbon is formed from the cross-linked synthetic resin. The pyrolysis is performed in an inert atmosphere, nitrogen or argon serving, for example, as the protective gas. The pyrolysis temperature is in general between 700° and 2000° C., and preferably at about 1100° C. The heating takes place at a temperature rate of about 40° C./hour to the pyrolysis temperature, and the final temperature is maintained for 5 hours. After the pyrolysis which generally takes place in a tubular furnace, the cooling down process takes place at the rate of 50° C./hour. The electrode blank then determines the final form of the electrode if the isotropic linear shrinkage of the material which takes place during the pyrolysis, of about 20%, is taken into consideration.

The manufacturing process of the electrodes can be followed by an activation procedure. Here, the electrodes may be heated, following the pyrolysis, for example, in air to a temperature of 450° to 500° C. (duration: about 1 hour). Through activation, a surface with a microporous structure is obtained which has a very advantageous effect on the electrical properties of the electrodes. The electrode blanks manufactured by the method of this invention exhibit a completely smooth homogeneous surface which can clearly be seen, for instance, from pictures taken with the scanning electron microscope (REM). This property is largely preserved during pyrolysis, and also after activation in air, the REM pictures show no visible changes of the surface structure.

From the electrodes prepared in accordance with the invention, capacities of 5 mF are measured at 1 Hz or 100 μF at 1 kHz in a physiological salt solution (pH=7). These capacities are sufficient for implantation purposes. With an electrode surface of 0.1 cm$^2$, the area capacity therefore reaches a value of 50 mF cm$^{-2}$ at 1 Hz, which indicates a very fine uniform microporosity.

This invention has been described in terms of specific embodiments set forth in detail, but it should be understood that these are by way of illustration only and that the invention is not necessarily limited thereto. Modifications and variations will be apparent from the disclosure and may be resorted to without departing from the spirit of the invention. Accordingly, such variations and modifications are considered to be within the scope of the invention and the following claims.

What is claimed is:

1. A method for preparing implantable electrodes having an electrode head and stem of vitreous carbon comprising the steps of:
   (a) preparing a hardened resin precondensate electrode stem blank; and
   (b) in a casting mold, casting a resin precondensate electrode head onto said electrode stem blank and cross-linking the cast electrode head; and
   (c) hardening the cross-linked electrode head; and
   (d) converting the resins of said hardenened electrode head and said hardened electrode stem blank into vitreous carbon by pyrolysis to provide a smooth surfaced vitreous carbon electrode head.

2. The method according to claim 1 further comprising the step of activating the electrode produced by the method of claim 1 to provide said electrode with a microporous surface.

3. The method according to claim 2 wherein said activation comprises the step of heating said electrode in air to provide said microporous surface.

4. The method according to claim 1 wherein the mold is formed of a non-wettable synthetic material.

5. The method according to claim 2 wherein the mold is formed of a non-wettable synthetic material.

6. The method according to claim 1 wherein the mold is formed from gold-plated alloy steel.

7. The method according to claim 2 wherein the mold is formed from gold-plated alloy steel.

8. The method according to claim 1 wherein said stem and said cross-linked head, prior to pyrolysis, are formed from precondensated furfuryl alcohol.

9. The method according to claim 2 wherein said stem and said cross-linked head, prior to pyrolysis, are formed from precondensated furfuryl alcohol.

10. The method according to claim 4 wherein said stem and said cross-linked head, prior to pyrolysis, are formed from precondensated furfuryl alcohol.

11. The method according to claim 5 wherein said stem and said cross-linked head, prior to pyrolysis, are formed from precondensated furfuryl alcohol.

12. The method according to claim 6 wherein said stem and said cross-linked head, prior to pyrolysis, are formed from precondensated furfuryl alcohol.

13. The method according to claim 7 wherein said stem and said cross-linked head, prior to pyrolysis, are formed from precondensated furfuryl alcohol.

14. The method according to claim 4 wherein said non-wettable synthetic material is silicone.

15. The method according to claim 5 wherein said non-wettable synthetic material is silicone.

16. The method according to claim 14 wherein prior to pyrolysis said stem and head are formed from precondensated furfuryl alcohol.

17. The method according to claim 15 wherein prior to pyrolysis said stem and head are formed from precondensated furfuryl alcohol.

* * * * *